US012685328B2

(12) United States Patent
Toyonaga et al.

(10) Patent No.: US 12,685,328 B2
(45) Date of Patent: Jul. 21, 2026

(54) METHOD FOR PRODUCING HYDROGEN GAS-CONTAINING MATERIAL AND DEVICE FOR PRODUCING HYDROGEN GAS-CONTAINING MATERIAL

(71) Applicant: Shinryo Corporation, Kita Kyushu (JP)

(72) Inventors: Ken Toyonaga, Kita Kyushu (JP); Yuu Shibahara, Kita Kyushu (JP); Kazumi Inoue, Kita Kyushu (JP); Yukihito Suetsugu, Kita Kyushu (JP); Daisuke Nishio, Kita Kyushu (JP); Hirokazu Toyoshima, Kita Kyushu (JP); Tooru Takeda, Kita Kyushu (JP)

(73) Assignee: Shinryo Corporation, Kita Kyushu (JP)

( * ) Notice: Subject to any disclaimer, the term of this patent is extended or adjusted under 35 U.S.C. 154(b) by 1549 days.

(21) Appl. No.: 16/474,315

(22) PCT Filed: Jan. 9, 2018

(86) PCT No.: PCT/JP2018/000168
§ 371 (c)(1),
(2) Date: Jun. 27, 2019

(87) PCT Pub. No.: WO2018/131559
PCT Pub. Date: Jul. 19, 2018

(65) Prior Publication Data
US 2019/0335795 A1     Nov. 7, 2019

(30) Foreign Application Priority Data
Jan. 12, 2017     (JP) ................................. 2017-002992

(51) Int. Cl.
*A23L 29/20*          (2016.01)
*A23L 33/10*          (2016.01)
(Continued)

(52) U.S. Cl.
CPC ............... *A23L 29/20* (2016.08); *A23L 33/10* (2016.08); *B01F 23/02* (2022.01); *B01F 23/20* (2022.01);
(Continued)

(58) Field of Classification Search
CPC . A23L 29/20; A23L 33/10; A23L 5/00; A23L 3/363; B01F 23/02; B01F 23/20;
(Continued)

(56) References Cited

U.S. PATENT DOCUMENTS 3,826,829 A * 7/1974 Marulich .............. A23L 29/206
                                                                 426/660
4,197,325 A * 4/1980 Ono ....................... A23L 29/284
                                                                 426/573
(Continued)

FOREIGN PATENT DOCUMENTS

CN          105982038 A * 10/2016 ............. A23L 21/18
CN          109640706 A * 4/2019 ........... A23L 33/155
(Continued)

OTHER PUBLICATIONS

"Safe use of hydrogen" Office of Energy Efficiency & Renewable Energy published Dec. 5, 2015 accessed at <https://web.archive.org/web/20151205031126/https://www.energy.gov/eere/fuelcells/safe-use-hydrogen> (Year: 2015).*
(Continued)

*Primary Examiner* — Stephen Hobson
(74) *Attorney, Agent, or Firm* — Oblon, McClelland, Maier & Neustadt, L.L.P.

(57)          ABSTRACT

There are provided a method for producing a hydrogen gas-containing material in which higher safety than in a production method of the related art is secured and which is simple and has high production efficiency, and a method for producing a hydrogen gas-containing material and a device
(Continued)

for producing a hydrogen gas-containing material in which it is possible to prevent nitrogen gas from being mixed into the hydrogen gas-containing material produced by the production method and it is easy to control an amount of hydrogen contained in the hydrogen gas-containing material. As one aspect, there is provided a method for producing a hydrogen gas-containing material including mixing a liquid composition containing a gelling agent or a thickener and a liquid medium with hydrogen gas in a line mixer (20) and cooling the liquid composition containing hydrogen gas in a liquid-transfer pipe (22) connected to the line mixer (20) and causing the liquid composition containing hydrogen gas to gel or thicken.

12 Claims, 3 Drawing Sheets

(51) Int. Cl.

| | |
|---|---|
| *B01F 23/00* | (2022.01) |
| *B01F 23/20* | (2022.01) |
| *B01J 10/00* | (2006.01) |
| *B01J 13/00* | (2006.01) |
| *B01J 20/02* | (2006.01) |
| *B01J 37/00* | (2006.01) |
| *B01J 37/18* | (2006.01) |
| *A23L 2/54* | (2006.01) |
| *A61K 8/19* | (2006.01) |
| *A61K 8/73* | (2006.01) |
| *B01F 25/42* | (2022.01) |

(52) U.S. Cl.
CPC ........... *B01J 10/00* (2013.01); *B01J 13/0052* (2013.01); *B01J 20/02* (2013.01); *B01J 37/0018* (2013.01); *B01J 37/18* (2013.01); *A23L 2/54* (2013.01); *A61K 8/19* (2013.01); *A61K 8/73* (2013.01); *A61K 2800/48* (2013.01); *B01F 25/42* (2022.01); *B01J 13/0065* (2013.01)

(58) Field of Classification Search
CPC ........ B01F 25/42; B01J 10/00; B01J 13/0052; B01J 20/02; B01J 37/0018; B01J 37/18; B01J 13/0065; A61K 8/19; A61K 8/73; A61K 2800/48; A61P 39/06; A61P 17/18; A61Q 19/00
See application file for complete search history.

(56) References Cited

U.S. PATENT DOCUMENTS

| | | | | |
|---|---|---|---|---|
| 4,676,283 | A * | 6/1987 | Caldwell | B01F 35/7176 261/DIG. 7 |
| 4,723,688 | A * | 2/1988 | Munoz | B67D 3/0009 222/88 |
| 4,919,960 | A * | 4/1990 | Ahmed | A23C 9/1542 426/477 |
| 6,065,303 | A * | 5/2000 | Harris | F25D 31/007 62/457.4 |
| 6,962,104 | B1 * | 11/2005 | Podlucky | A47J 31/18 99/275 |
| 7,703,382 | B2 * | 4/2010 | Oranski | B67D 1/0888 99/295 |
| 10,953,041 | B2 * | 3/2021 | Levy | A61K 8/19 |
| 2005/0260329 | A1 * | 11/2005 | Yusuf | A23G 3/0072 426/660 |
| 2006/0112831 | A1 * | 6/2006 | Greenwald | A47J 31/56 99/275 |
| 2007/0257378 | A1 * | 11/2007 | Spiegel | B01F 23/2363 261/DIG. 7 |
| 2009/0285965 | A1 * | 11/2009 | Liu | A23L 2/66 426/590 |
| 2010/0219260 | A1 * | 9/2010 | Matsuoka | B01F 23/23764 261/78.2 |
| 2010/0234784 | A1 * | 9/2010 | Hartwell | A61P 17/02 424/770 |
| 2010/0251901 | A1 * | 10/2010 | Santoiemmo | B01F 21/22 99/323.2 |
| 2010/0269707 | A1 * | 10/2010 | Wiemer | B67D 1/0021 99/323.1 |
| 2011/0041543 | A1 * | 2/2011 | Tachibana | B67D 1/0057 62/340 |
| 2011/0042414 | A1 * | 2/2011 | Tachibana | B67D 1/0864 222/129.1 |
| 2012/0070540 | A1 * | 3/2012 | Igarashi | C02F 9/00 426/67 |
| 2012/0128749 | A1 * | 5/2012 | Tsuji | A61P 31/04 510/438 |
| 2013/0037973 | A1 * | 2/2013 | Lavaque | B01F 23/2362 261/27 |
| 2013/0043124 | A1 * | 2/2013 | Park | A47J 47/01 204/263 |
| 2013/0108515 | A1 * | 5/2013 | Satoh | C01B 3/344 422/162 |
| 2014/0234488 | A1 * | 8/2014 | Chang | C12G 3/06 426/62 |
| 2014/0374443 | A1 * | 12/2014 | Young | B67D 1/0857 222/105 |
| 2015/0239760 | A1 * | 8/2015 | Kim | C25B 9/17 210/192 |
| 2016/0249668 | A1 * | 9/2016 | Igarashi | A23F 3/163 426/72 |
| 2016/0318746 | A1 * | 11/2016 | Peirsman | B67D 1/005 |
| 2017/0080022 | A1 * | 3/2017 | Levy | A61K 9/0095 |
| 2019/0029927 | A1 * | 1/2019 | Takeda | A61K 9/0087 |
| 2019/0297931 | A1 * | 10/2019 | Koch | A23K 20/163 |

FOREIGN PATENT DOCUMENTS

| | | | | |
|---|---|---|---|---|
| EP | 0117011 | A1 * | 8/1984 | A23C 9/1236 |
| EP | 0 684 771 | 81 | 9/1997 | |
| EP | 2 653 037 | A1 | 10/2013 | |
| JP | 54-22501 | B | 8/1979 | |
| JP | 4-36662 | B2 | 6/1992 | |
| JP | 2749211 | 82 | 2/1998 | |
| JP | 11-290002 | A | 10/1999 | |
| JP | 2001-211839 | A | 8/2001 | |
| JP | 2003-145175 | A | 5/2003 | |
| JP | 2003-231892 | A | 8/2003 | |
| JP | 3106002 | U | 12/2004 | |
| JP | 2005-245427 | A | 9/2005 | |
| JP | 2007-236299 | A | 9/2007 | |
| JP | 2007-31 4496 | A | 12/2007 | |
| JP | 3139460 | U | 2/2008 | |
| JP | 2009165459 | | * 7/2009 | |
| JP | 2009165459 | A | * 7/2009 | |
| JP | 2011-57659 | A | 3/2011 | |
| JP | 2011057659 | A | * 3/2011 | |
| JP | 2011-211964 | A | 10/2011 | |
| JP | 2011-245471 | A | 12/2011 | |
| JP | 2012-147757 | A | 8/2012 | |
| JP | 2013017944 | A | * 1/2013 | |
| JP | 2017121232 | A | * 7/2017 | |
| JP | 2017-192376 | A | 10/2017 | |
| KR | 10-1244629 | B1 | 3/2013 | |
| KR | 10-2018-0130542 | A | 12/2018 | |
| WO | WO-9619925 | A1 * | 7/1996 | A23L 2/54 |
| WO | WO-9804158 | A1 * | 2/1998 | A23L 2/62 |
| WO | WO-2011018865 | A1 * | 2/2011 | A61P 43/00 |
| WO | WO-2011069884 | A1 * | 6/2011 | A23L 29/284 |
| WO | WO-2011069979 | A1 * | 6/2011 | A23C 9/1524 |
| WO | WO-2014058867 | A1 * | 4/2014 | C07C 67/333 |
| WO | WO-2014184245 | A1 * | 11/2014 | A23L 29/284 |

(56)     References Cited

FOREIGN PATENT DOCUMENTS

WO     WO-2015156359 A1 * 10/2015     ............. A23L 29/20
WO     WO-2019022126 A1 *  1/2019     ............. A23L 29/20
WO     WO-2020065240 A1 *  4/2020     ............. A23C 19/14

OTHER PUBLICATIONS

Epo translation of WO-2015156359-A1 (Year: 2015).*

Notice of Allowance issued Apr. 23, 2021 in Korean Patent Application No. 10-20197018629 (with English translation), 5 pages.

Korean Office Action issued Oct. 23, 2020 in Korean Patent Application No. 10-2019-7018629 (with English translation), 16 pages.

International Search Report issued Apr. 17, 2018 in PCT/JP2018/000168 filed Jan. 9, 2018.

Japanese Office Action issued Jan. 8, 2019 in Japanese Patent Application No. 2018-561358 (with unedited computer- generated English translation), 4 pages.

* cited by examiner

METHOD FOR PRODUCING HYDROGEN GAS-CONTAINING MATERIAL AND DEVICE FOR PRODUCING HYDROGEN GAS-CONTAINING MATERIAL

TECHNICAL FIELD

The present invention relates to a method for producing a hydrogen gas-containing material and a device for producing a hydrogen gas-containing material.

Priority is claimed on Japanese Patent Application No. 2017-002992, filed on Jan. 12, 2017, the content of which is incorporated herein by reference.

BACKGROUND ART

In recent years, various functions of hydrogen gas such as a function of neutralizing a peroxide substance in a living body and a function of improving biological activity have been focused on. Therefore, food, beverages, cosmetics, and the like which contain hydrogen gas have been proposed.

Regarding a method for producing food containing hydrogen gas, a method in which a food material in a sol state is put into a container, sealing is performed with a sealing lid, and nitrogen gas is then blown into the container in order to remove internal air, air (oxygen) in the container is completely ejected, hydrogen gas is then blown thereinto, and a food material in a sol state and hydrogen gas are mixed, and then cooled and gelled, has been disclosed (Patent Document 1).

CITATION LIST

Patent Document

[Patent Document 1]
Japanese Unexamined Patent Application, First Publication No. 2009-165459

SUMMARY OF THE INVENTION

Problem to be Solved by the Invention

When hydrogen gas is mixed with a food material while hydrogen gas is blown into a container, there is a risk of a ratio between hydrogen gas and oxygen gas in a gas phase in the container coming into an explosive range and a fire starting. Therefore, in the method described in Patent Document 1, when nitrogen gas in a gas phase is blown into the container sealed with a sealing lid, oxygen gas in a gas phase is exhausted to form nitrogen gas sealing, and hydrogen gas is then blown into the food material in the container.

However, in the method described in Patent Document 1, since nitrogen gas is contained in the container of a gas phase, nitrogen is mixed into a food material in a sol state from the gas phase, and accordingly, the purity and content of hydrogen gas are thus thought to be lowered.

In addition, in the method described in Patent Document 1, a gas with the same volume as the blown hydrogen gas is exhausted from an exhaust port provided on a sealing lid. Since hydrogen gas is contained in gas exhausted from the exhaust port, a ratio between hydrogen gas and oxygen gas in the surroundings of the container may be brought within an explosive range, and there is then a risk of fire. Therefore, in the method described in Patent Document 1, a detection device such as a hydrogen gas sensor should be provided in the surroundings of the container, and the method described in Patent Document 1 is not simple.

In addition, since the method described in Patent Document 1 is a so-called batch type production method, in order to resume production of a food material after one food material is produced, the obtained food material is removed from the container and raw materials are then prepared, and it is necessary to mix it with hydrogen gas, and there is room for improvement in terms of production efficiency.

The present invention has been made in view of the above circumstances, and provides a method for producing a hydrogen gas-containing material in which higher safety than in a production method of the related art is secured and which is simple and has high production efficiency, and in which it is possible to prevent an unnecessary gas containing nitrogen gas from being mixed into the hydrogen gas-containing material produced by the production method, and it is easy to adjust an amount of hydrogen contained in the hydrogen gas-containing material, and a production device in which higher safety than in a production device of the related art is secured and it is possible to produce a hydrogen gas-containing material and which is simple and has high production efficiency, and which is a device for producing a hydrogen gas-containing material in which it is possible to prevent an unnecessary gas containing nitrogen gas from being mixed into the hydrogen gas-containing material produced by the production device and it is easy to adjust an amount of hydrogen contained in the hydrogen gas-containing material.

Means for Solving Problem

The present invention includes the following aspects.

[1] A method for producing a hydrogen gas-containing material, including:

mixing a liquid composition containing a gelling agent or a thickener and a liquid medium with hydrogen gas in a line mixer; and cooling the liquid composition containing hydrogen gas in a liquid-transfer pipe connected to the line mixer and causing the liquid composition containing hydrogen gas to be gelled or thickened.

[2] The method for producing a hydrogen gas-containing material according to [1], wherein the liquid composition containing hydrogen gas in the liquid-transfer pipe is cooled using a cooler.

[3] The method for producing a hydrogen gas-containing material according to [1] or [2], wherein the liquid composition is transferred as a liquid to the line mixer using a pump.

[4] The method for producing a hydrogen gas-containing material according to any of [1] to [3], further including:

filling the hydrogen gas-containing material into the filling container using a filling device connected to an end part of the liquid-transfer pipe.

[5] A device for producing a hydrogen gas-containing material, including:

a line mixer in which a liquid composition containing a gelling agent or a thickener and a liquid medium, and hydrogen gas are mixed; and a cooler that cools the liquid composition containing hydrogen gas in a liquid-transfer pipe connected to the line mixer.

[6] The device for producing a hydrogen gas-containing material according to [5], including a pump that transfers the liquid composition as a liquid to the line mixer.

[7] The device for producing a hydrogen gas-containing material according to [5] or [6], wherein a filling device for filling the hydrogen gas-containing material is connected to an end part of the liquid-transfer pipe.

[8] A method for producing a hydrogen gas-containing material, including:

mixing a liquid composition containing a gelling agent or a thickener and a liquid medium with hydrogen gas in a first line mixer; and mixing the liquid composition containing hydrogen gas with a reactant that causes the liquid composition containing hydrogen gas to be gelled or thickened in a second line mixer, and causing the liquid composition containing hydrogen gas to be gelled or thickened.

[9] The method for producing a hydrogen gas-containing material according to [8], wherein the liquid composition is transferred as a liquid to the first line mixer using a pump.

[10] The method for producing a hydrogen gas-containing material according to [8] or [9], further including filling the hydrogen gas-containing material into a filling container using a filling device connected to an end part of a liquid-transfer pipe connected to the second line mixer.

[11] A device for producing a hydrogen gas-containing material, including:

a first line mixer in which a liquid composition containing a gelling agent or a thickener and a liquid medium and hydrogen gas are mixed; and a second line mixer in which the liquid composition containing hydrogen gas and a reactant that causes the liquid composition containing hydrogen gas to be gelled or thickened are mixed, wherein the first line mixer and the second line mixer are connected.

[12] The device for producing a hydrogen gas-containing material according to [11], including a pump for performing liquid transfer of the liquid composition to the first line mixer.

[13] The device for producing a hydrogen gas-containing material according to [11] or [12], wherein a filling device for filling the hydrogen gas-containing material is connected to an end part of a liquid-transfer pipe connected to the second line mixer.

[14] The method for producing a hydrogen gas-containing material according to any of [1] to [4], wherein the liquid composition in which a gelling agent or a thickener and a liquid medium are mixed in in the line mixer and hydrogen gas are mixed in in the line mixer.

[15] The method for producing a hydrogen gas-containing material according to [14], wherein the liquid composition obtained by mixing a gelling agent or a thickener and a liquid medium and performing circulating through a circulation path including the line mixer is mixed with hydrogen gas in the line mixer.

[16] The method for producing a hydrogen gas-containing material according to any of [8] to [10], wherein the liquid composition obtained by mixing a gelling agent or a thickener and a liquid medium in in the first line mixer is mixed with hydrogen gas in the first line mixer.

[17] The method for producing a hydrogen gas-containing material according to [16], wherein the liquid composition obtained by mixing a gelling agent or a thickener and a liquid medium and performing circulating through a circulation path including the first line mixer is mixed with hydrogen gas in the first line mixer.

[18] The device for producing a hydrogen gas-containing material according to any of [5] to [7], wherein the line mixer is in a circulation path.

[19] The device for producing a hydrogen gas-containing material according to [18], including a line switching unit for switching liquid transfer to the circulation path to liquid transfer to the liquid-transfer pipe.

[20] The device for producing a hydrogen gas-containing material according to any of [11] to [13], wherein the first line mixer is in a circulation path.

[21] The device for producing a hydrogen gas-containing material according to [20], including a line switching unit for switching liquid transfer to the circulation path to liquid transfer to the liquid-transfer pipe.

Effects of Invention

According to the method for producing a hydrogen gas-containing material of the present invention, it is possible to produce a hydrogen gas-containing material simply and efficiently while securing higher safety than in a production method of the related art.

According to the method for producing a hydrogen gas-containing material of the present invention, it is possible to produce a hydrogen gas-containing material with a reduced amount of an unnecessary gas containing nitrogen gas mixed in. In addition, according to the method for producing a hydrogen gas-containing material of the present invention, it is easy to adjust an amount of hydrogen contained in the hydrogen gas-containing material.

According to the device for producing a hydrogen gas-containing material of the present invention, it is possible to produce a hydrogen gas-containing material simply and efficiently while securing higher safety than in a production method of the related art.

According to the device for producing a hydrogen gas-containing material of the present invention, it is possible to produce a hydrogen gas-containing material with a reduced amount of an unnecessary gas containing nitrogen gas mixed in. In addition, according to the device for producing a hydrogen gas-containing material of the present invention, it is easy to adjust an amount of hydrogen contained in the hydrogen gas-containing material.

MODE FOR CARRYING OUT OF THE INVENTION

Figure 1:
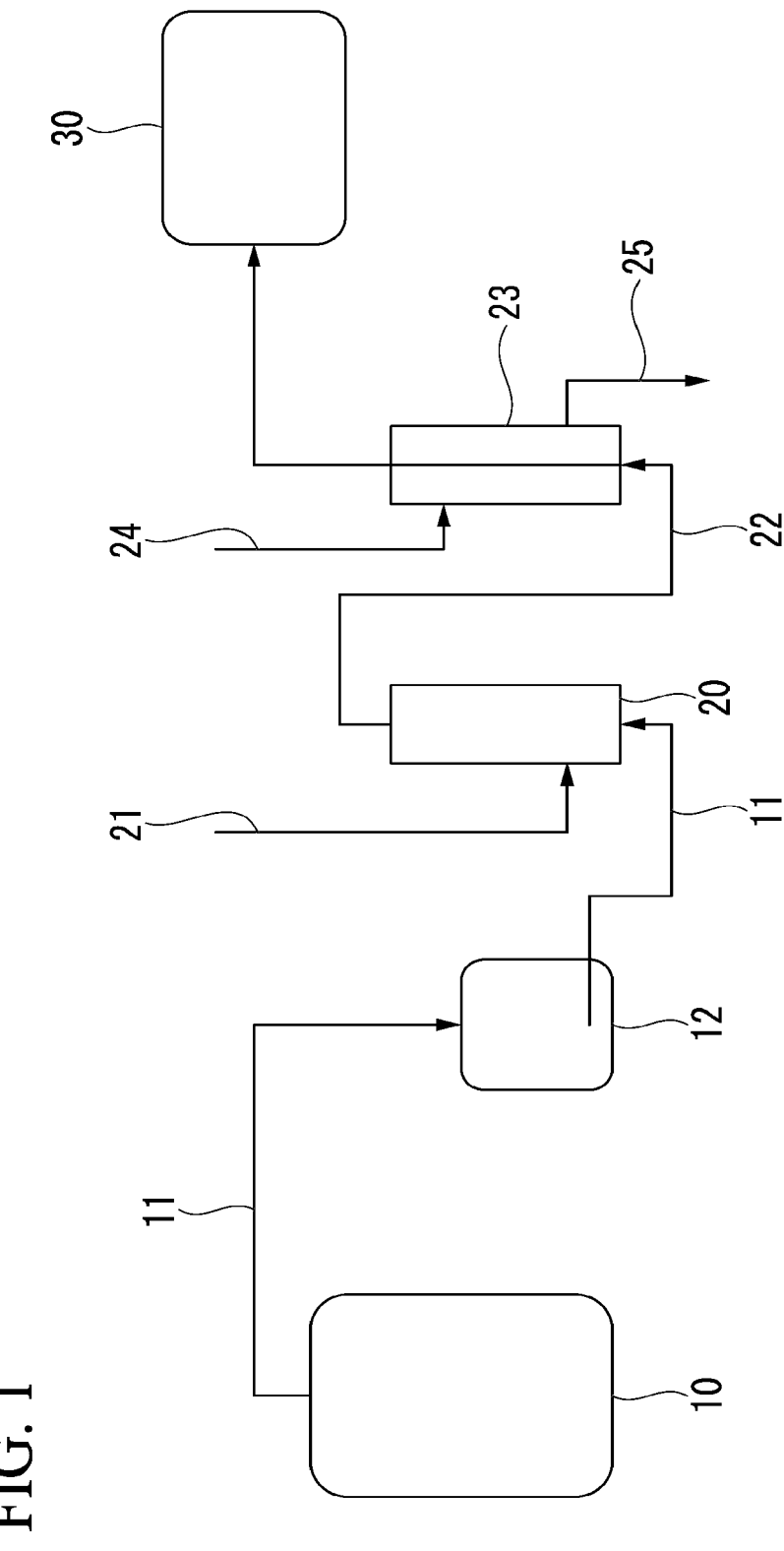
FIG. 1 is a schematic view illustrating a method for producing a hydrogen gas-containing material and a device for producing the same according to a first embodiment of the present invention.

Definitions of the following terms apply throughout this specification and claims.

"Gelling agent" refers to a compound that can form a network structure in which a liquid medium can be held by physical aggregation due to hydrogen bonding or the like or crosslinking due to covalent bonds or the like.

"Thickener" refers to a compound that can impart viscosity to a liquid medium.

"Liquid composition" refers to a composition containing a gelling agent or a thickener and a liquid medium that has not been subjected to gelling or thickening.

"Gel composition" refers to a composition obtained by gelling a liquid composition containing a gelling agent.

"Viscous composition" refers to a composition obtained by thickening a liquid composition containing a thickener.

"Gelling temperature" refers to a temperature at which, when a liquid composition is put into a 50 ml glass screw-closing bottle and heated to 75° C., and then gradually cooled, even if the screw-closing bottle is inclined by 45° or 90°, the liquid composition gels or thickens and does not flow.

"Reactant that causes a liquid composition to be gelled or thickened" refers to a compound having an effect of promoting formation of a network structure using the above gelling agent or increasing the viscosity using the above thickener and an aqueous solution thereof.

"Content (volume % [v/w]) of a hydrogen gas in a bubble state in the gel composition (viscous composition)" refers to a proportion of the volume ($cm^3$) of hydrogen gas in a bubble state contained in a predetermined mass (100 g) of the gel composition (viscous composition).

[Method for Producing a Hydrogen Gas-Containing Material]

(Liquid Composition)

First, respective components of a liquid composition used for a method for producing a hydrogen gas-containing material of the present invention will be described.

The liquid composition used for the method for producing a hydrogen gas-containing material of the present invention contains a gelling agent or a thickener, and further contains a liquid medium.

The gelling agent and the thickener contained in the liquid composition are not particularly limited and known substances can be used.

Specific examples of the gelling agent or the thickener include gelatin, agar, carrageenan, pectin, glucomannan, pullulan, alginic acid, alginates such as sodium alginate, potassium alginate, calcium alginate, and ammonium alginate, alginic acid derivatives such as propylene glycol alginate ester, and proteins or polysaccharides derived from natural products such as an aureobasidium culture solution, succinoglycan, linseed gum, arabic gum, arabinogalactan, welan gum, cassia gum, ghatti gum, curdlan, karaya gum, carob bean gum, xanthan gum, chitosan, guar gum, guar gum enzymatic degradation products, yeast cell walls, psyllium seed gum, artemisia sphaerocephala seed gum, gellan gum, tamarind seed gum, tara gum, dextran, tragacanth gum, abelmoschus manihot, microfibrous cellulose, furcellaran, colpomenia sinuosa extract, macrophomopsis gum, rhamsan gum, levan, okra extract, seaweed cellulose, brown algae extract, elephant roots extract, sweetpotato cellulose, soybean polysaccharides, nata de coco, carboxymethylcellulose, and agarose; synthetic polymers such as a carboxyvinyl polymer, carboxyvinyl polymer derivatives, carboxymethylcellulose, polyvinyl alcohol, polyvinyl alcohol derivatives, polyvinyl pyrrolidone, polyvinyl pyrrolidone derivatives, polyhydroxyethyl methacrylate, polyacrylic acid, polystyrene sulfonic acid, and silicones (dimethicone, cyclic dimethicone, methyl phenyl polysiloxane, crosslinked dimethylpolysiloxane, methylsiloxane reticular polymers, polyether-modified silicones, acrylic-modified silicones, amethicone, etc.); and oily thickeners such as higher fatty acids, for example, myristic acid, palmitic acid, and stearic acid, and higher alcohols such as behenyl alcohol, stearyl alcohol, and cetyl alcohol. Such materials may be used alone or two or more thereof may be used in combination.

The liquid medium contained in the liquid composition is appropriately selected depending on applications of the obtained hydrogen gas-containing material and the type of the gelling agent or the thickener. For example, when used in the industrial and research fields of food, medicines, or cosmetics, water, an oily component, ethanol, or the like is preferably used, and when used in other industrial and research fields, any liquid medium containing an organic solvent may be used.

When a hydrogen gas-containing material is used in the fields of cell cultures, medicines, food, cosmetics, and the like, regarding an additive that may be added to a liquid composition, in order to exhibit a synergistic effect with existing effects or impart a new effect, any of known additives can be used as long as they are components that can be used together with components contained in the liquid composition.

Regarding the additive, any one or more of a food additive, a cosmetic additive, an antioxidant, a culture medium additive, and a feed additive may be included. Specific examples thereof include antimicrobials, water retention emulsion stabilizers, binders, quality modifiers, anti-adhesive agents, preservatives, antioxidants, and reinforcing agents such as vitamins, and amino acid derivatives, nucleic acids, lipids, antioxidants, anti-glycation agents, fats and oils, and surfactants.

The additives may be used alone or two or more thereof may be used in combination depending on a desired effect.

[Method for Producing a Hydrogen Gas-Containing Material and Device for Producing the Same According to the First Embodiment]

The method for producing a hydrogen gas-containing material of the present invention and the device for producing the same according to the first embodiment (hereinafter simply referred to as the "first embodiment") will be described.

The method for producing a hydrogen gas-containing material according to the first embodiment is a method for producing a hydrogen gas-containing material in which a liquid composition containing a gelling agent or a thickener and a liquid medium and hydrogen gas are mixed in in a line mixer, the liquid composition containing hydrogen gas is cooled in a liquid-transfer pipe connected to the line mixer, and the liquid composition containing hydrogen gas gels or thickens.

The production device according to the first embodiment of the present invention includes a line mixer for mixing a liquid composition containing a gelling agent or a thickener and a liquid medium with hydrogen gas and a cooler for cooling the liquid composition containing hydrogen gas in a liquid-transfer pipe connected to the line mixer.

The production device according to the first embodiment of the present invention is preferably a production device for performing the production method according to the first embodiment of the present invention.

FIG. 1 schematically shows the production device according to the first embodiment of the present invention as one aspect of the production device according to the first embodiment of the present invention. As shown in FIG. 1, the production device according to the first embodiment includes a preparation container 10 in which a liquid composition is prepared, a line mixer 20 in which a liquid composition and hydrogen gas are mixed, and a filling device 30 in which a gel composition or a viscous composition as a hydrogen gas-containing material is filled into a filling container. A hydrogen supply pipe 21 through which hydrogen gas is supplied to the line mixer 20 is connected to the line mixer 20.

A supply pipe 11 through which the liquid composition prepared in the preparation container 10 is supplied to the line mixer 20 is provided between the preparation container 10 and the line mixer 20. A liquid-transfer pipe 22 through which the liquid composition containing hydrogen gas mixed in in the line mixer 20 is transferred as a liquid to the filling device 30 is provided between the line mixer 20 and the filling device 30, and the filling device 30 is connected to the end part of the liquid-transfer pipe 22. A pump 12 by which the liquid composition prepared in the preparation container 10 is transferred as a liquid to the line mixer 20 is provided on the supply pipe 11. A cooler 23 that cools a supply pipe 22 from the surroundings and cools a liquid composition containing hydrogen gas in the liquid-transfer pipe 22 is provided on the liquid-transfer pipe 22. A cooling liquid supply pipe 24 through which a cooling liquid is supplied to the cooler 23 and a cooling liquid discharge pipe 25 through which a cooling liquid is discharged from the cooler 23 are provided on the cooler 23.

First, in the first embodiment of the present invention, the liquid composition prepared in the preparation container 10 shown in FIG. 1 and hydrogen gas are mixed in in the line mixer 20 (line mixing).

Regarding the gelling agent or thickener in the first embodiment of the present invention, a gelling agent or thickener that causes a liquid composition to gel or thicken by cooling is used. Specific examples of such a gelling agent or thickener include gelatin, agar, carrageenan, pectin, glucomannan, pullulan, alginic acid, alginates such as sodium alginate, potassium alginate, calcium alginate, and ammonium alginate, alginic acid derivatives such as propylene glycol alginate ester, an aureobasidium culture solution, succinoglycan, linseed gum, arabic gum, arabinogalactan, welan gum, cassia gum, ghatti gum, curdlan, karaya gum, carob bean gum, xanthan gum, chitosan, guar gum, guar gum enzymatic degradation products, yeast cell walls, psyllium seed gum, artemisia sphaerocephala seed gum, gellan gum, tamarind seed gum, tara gum, dextran, tragacanth gum, abelmoschus manihot, microfibrous cellulose, furcellaran, colpomenia sinuosa extract, macrophomopsis gum, rhamsan gum, levan, okra extract, seaweed cellulose, brown algae extract, elephant roots extract, sweetpotato cellulose, soybean polysaccharides, nata de coco, carboxymethylcellulose, and agarose, oily thickeners such as higher fatty acids, for example, myristic acid, palmitic acid, and stearic acid, and higher alcohols, for example, behenyl alcohol, stearyl alcohol, and cetyl alcohol, but not limited thereto.

Regarding such a gelling agent or thickener, one, two or more selected from among gelatin, agar, carrageenan, pectin, glucomannan, pullulan, alginic acid, alginate, alginic acid derivatives, an aureobasidium culture solution, succinoglycan, linseed gum, arabic gum, arabinogalactan, welan gum, cassia gum, ghatti gum, curdlan, karaya gum, carob bean gum, xanthan gum, chitosan, guar gum, guar gum enzymatic degradation products, yeast cell walls, psyllium seed gum, artemisia sphaerocephala seed gum, gellan gum, tamarind seed gum, tara gum, dextran, tragacanth gum, abelmoschus manihot, microfibrous cellulose, furcellaran, a colpomenia sinuosa extract, macrophomopsis gum, rhamsan gum, levan, an okra extract, seaweed cellulose, a brown algae extract, elephant roots extract, sweetpotato cellulose, soybean polysaccharides, nata de coco, carboxymethylcellulose, agarose, higher fatty acids, and higher alcohols are preferable, one, two or more selected from among gelatin, agar, carrageenan, pectin, guar gum, tamarind gum, glucomannan, carob bean gum, xanthan gum, pullulan, carboxymethylcellulose, alginic acid, alginate, alginic acid derivatives, higher fatty acids, and higher alcohols are more preferable, and one, two or more selected from among gelatin, higher fatty acids, and higher alcohols are still more preferable.

In preparation of a liquid composition, a liquid medium such as water or an organic solvent is put into the preparation container 10, and raw materials containing a gelling agent or a thickener are then put thereinto while stirring, and heating can be performed to a temperature higher than a gelling temperature or a temperature at which thickening is prevented, but not limited thereto.

The preparation container 10 may be appropriately selected according to a gelling agent or thickener to be used. For example, it may be selected in consideration of the heat resistance of the container and the corrosion resistance with respect to the liquid composition. Regarding a member of which the preparation container 10 is constituted, although device materials such as SUS, glass linings, fluororesin linings, and plastics, may be used therefore, there is no limitation thereto.

When a liquid composition containing a gelling agent is used as the liquid composition in the first embodiment of the present invention, the temperature of the liquid composition is maintained at a temperature higher than a gelling temperature from preparation until it is mixed with hydrogen gas. On the other hand, when a liquid composition containing a thickener is used as the liquid composition, the temperature of the liquid composition is maintained at a temperature at which thickening is prevented before mixing with hydrogen gas from preparation.

The liquid composition prepared in the preparation container 10 is supplied to the line mixer 20 via the supply pipe 11. In addition, hydrogen gas is supplied to the line mixer 20 via the hydrogen supply pipe 21. Here, a method for supplying hydrogen gas to the line mixer 20 is not particularly limited.

In the first embodiment of the present invention, the pump 12 is used when a liquid composition is supplied from the preparation container 10 to the line mixer 20. The pump 12 may be a known pump having a function of adjusting a pressure of a liquid composition that flows through the supply pipe 11 or may be a pressure pump or a decompression pump.

The liquid composition is supplied from the preparation container 10 to the line mixer 20 via the supply pipe 11 using the pump 12, and thus an amount of hydrogen gas dispersed in the liquid composition containing hydrogen gas is easily controlled.

Regarding the pump, a pressure pump or a decompression pump is preferable, and a pressure pump is more preferable. Examples of such a pump include a turbo pump by which a rotating component imparts energy to a fluid and a volumetric pump by which energy is imparted to a fluid due to change its volume, but not limited thereto.

Examples of a turbo pump include a centrifugal pump such as a spiral pump and a diffuser, and a diagonal flow pump, and an axial flow pump.

Examples of the positive displacement pump include a reciprocating pump such as a piston pump, a plunger pump, and a diaphragm pump and a rotary pump such as a gear pump, a rotary pump, a sine pump, a vane pump, and a screw pump.

A turbo pump or a volumetric pump is preferable, and a gear pump, a rotary pump, a sine pump, a vane pump, or a screw pump which is suitable for a high-viscosity fluid, has high quantitative performance, and low flow rate fluctuation is more preferable.

A ratio between the volume of the liquid composition and the volume of hydrogen gas supplied to the line mixer 20 is appropriately set according to a desired content of hydrogen gas and a gelling agent or thickener to be used for a hydrogen gas-containing material obtained in the method for producing a hydrogen gas-containing material of the present invention.

Such a ratio between the volume of the liquid composition and the volume of hydrogen gas supplied to the line mixer 20 is preferably 0.01 to 2.0, more preferably 0.05 to 1.8, and still more preferably 0.1 to 1.5.

Here, the "ratio between the volume of the liquid composition and the volume of hydrogen gas supplied to the line mixer" is a value obtained according to (flow rate of hydrogen gas)/(flow rate of the liquid composition supplied to the line mixer 20).

Mixing of a liquid composition and hydrogen gas is preferably performed without exposing the liquid composition to outside air.

Regarding the line mixer 20, a known line mixer having a function and form that can perform mixing without exposing the liquid composition and hydrogen gas to outside air can be used. As a specific example, a Homomic Line Flow 30 type which is a homo mixer (commercially available from PRIMIX Corporation) can be used, but not limited thereto.

Examples of such a line mixer include a static mixer that generates swirling and turbulence by providing an obstacle in the flow path, a homogenizer including a mechanism in which a movable part shears a fluid in the flow path, and a dynamic mixer such as a homo mixer, but not limited thereto. In addition, a pump having the same function may he used without limitation to those called a mixer. Such a mixer may he used alone or two or more thereof may be used in combination.

Regarding the line mixer, a static mixer or a dynamic mixer is preferable, and in consideration of support of a high-viscosity fluid, a dynamic mixer is more preferable and a homo mixer is still more preferable.

Next, in the first embodiment of the present invention, in the liquid-transfer pipe 22 connected to the line mixer 20, a liquid composition containing hydrogen gas is cooled to gel or thicken.

When the liquid composition containing hydrogen gas contains a gelling agent, the liquid composition containing hydrogen gas is cooled in the liquid-transfer pipe 22 at a temperature lower than the gelling temperature, and when the liquid composition containing hydrogen gas contains a thickener, the liquid composition containing hydrogen gas is cooled in the liquid-transfer pipe 22 at a temperature lower than a temperature at which thickening is prevented. By cooling to such a temperature, the liquid composition containing hydrogen gas gels or thickens while hydrogen gas is contained, and becomes a gel composition containing hydrogen gas or a viscous composition containing hydrogen gas.

As shown in FIG. 1, in the first embodiment of the present invention, the liquid composition containing hydrogen gas in the liquid-transfer pipe 22 is cooled by the cooler 23. Preferably, the liquid composition containing hydrogen gas is cooled by the cooler 23 without exposing the liquid composition containing hydrogen gas to outside air. In addition, liquid transfer of the liquid composition containing hydrogen gas from the line mixer 20 to the cooler 23 is preferably performed without exposing the liquid composition containing hydrogen gas to outside air.

More specifically, a cooling liquid is supplied from the cooling liquid supply pipe 24 to the cooler 23 and cools the surroundings of the supply pipe 22. The cooling liquid used for cooling flows through the cooling liquid discharge pipe 25 and is discharged from the cooler 23. Regarding the cooler 23, for example, a jacket may be attached to the liquid-transfer pipe 22 and a cooling liquid may circulate in the jacket, but not limited thereto as long as hydrogen gas does not leak to the outside of the liquid-transfer pipe 22.

Examples of such a cooling method include a cooling method such as air cooling without using a cooler and a cooling method using a cooler. Regarding the cooling method, air cooling or cooling using a cooler is preferable and cooling using a cooler is more preferable.

Examples of such a cooler include a plate type cooler in which a fluid with a temperature difference alternately flows between a plurality of stacked plates, a spiral type cooler in which a flow path of a fluid is spiral, a shell and tube type cooler in a form in which a plurality of heat transfer tubes pass through a closed cylinder called a shell, a fin tube type cooler in which fins for increasing a heat transfer area are attached to the outside of a heat transfer tube, a double tube type cooler in which a refrigerant flows through a jacket flow path around a pipe, a multi-cylindrical cooler, a multi-circular tube type cooler, a tank oil type cooler, and an air cooling type cooler, but not limited thereto. Such a cooler may be used alone or two or more thereof may be used in combination.

Regarding the cooler, one selected from among a plate type cooler, a spiral type cooler, a shell and tube type cooler, a fin tube type cooler, a double tube type cooler, a multi-tubular cylindrical cooler, a multi-circular tube type cooler, a tank oil type cooler and an air cooling type cooler or a combination of two or more thereof is preferable, and a double tube type cooler is more preferable.

Regarding the low-temperature-side fluid used for a cooler, a liquid or a gas can be used, and a liquid or a gas is preferable, and a liquid is more preferable.

The gel composition containing hydrogen gas or the viscous composition containing hydrogen gas in the liquid-transfer pipe 22 is supplied to the filling device 30 connected to the end part of the liquid-transfer pipe 22 and filled into a filling container by the filling device 30. When the filling device 30 is connected to the end part of the liquid-transfer pipe 22, it is easy to prevent a gas other than hydrogen gas from being mixed into the gel composition or the viscous composition.

Liquid transfer of the gelled or thickened liquid composition containing hydrogen gas, that is, the gel composition containing hydrogen gas or the viscous composition containing hydrogen gas, from the cooler 23 to the filling device 30 is preferably performed without exposing the gelled or thickened liquid composition containing hydrogen gas to outside air.

Regarding a filling method, preferably, filling is performed in a filling container so that as little gas phase space as possible occurs and sealing is quickly performed. Quick sealing is preferable because an amount of volatilization of hydrogen gas to outside air is reduced. A sealing method depends on the type of the filling container, and known sealing methods such as heat sealing and use of a lid with an inner lid may be exemplified.

The material of the filling container is preferably a material through which it is difficult for hydrogen gas to permeate in order to prevent loss due to permeation of hydrogen gas. Specific examples include a pouch having an aluminum foil, an organic polymer sheet or film through which it is difficult for hydrogen gas to permeate, a composite material thereof and a metal container, but not limited thereto as long as it is a material through which it is difficult for hydrogen gas to permeate.

(Actions and Effects of the First Embodiment)

As described above, in the method according to the first embodiment of the present invention, a liquid composition and hydrogen gas are nixed in in a line mixer, and a liquid composition containing hydrogen gas is cooled and gels or thickens in the liquid-transfer pipe connected to the line mixer. Therefore, since hydrogen gas does not leak to the outside air, a ratio between hydrogen gas and oxygen gas in the gas phase around the device is not within an explosive range, and a risk of fire is significantly reduced. In addition, since hydrogen gas is mixed in in the line mixer, an amount of an unnecessary gas containing nitrogen gas mixed into the hydrogen gas-containing material is reduced and the quality of the hydrogen gas-containing material is improved. In addition, since there is no need to provide a gas sensor, mixing is performed in a line mixer for a short time, and a hydrogen gas-containing material can be continuously produced, it is possible to produce a hydrogen gas-containing material simply and efficiently according to a production method in the related art and it is easy to control an amount of hydrogen contained in the hydrogen gas-containing material.

[Method for Producing a Hydrogen Gas-Containing Material and Device for Producing the Same According to the Second Embodiment]

A method for producing a hydrogen gas-containing material of the present invention and a device for producing the same according to the second embodiment (hereinafter simply referred to as the "second embodiment") will be described.

The method for producing a hydrogen gas-containing material according to the second embodiment is a method for producing a hydrogen gas-containing material in which a liquid composition containing a gelling agent or a thickener and a liquid medium and hydrogen gas are mixed in in a first line mixer, the liquid composition containing hydrogen gas and a reactant that causes a liquid composition to gel or thicken (hereinafter simply referred to as a "reactant") are mixed in in a second line mixer, and thus the liquid composition containing hydrogen gas gels or thickens.

The production device according to the second embodiment of the present invention includes a first line mixer in which a liquid composition containing a gelling agent or a thickener and a liquid medium and hydrogen gas are mixed, and a second line mixer in which the liquid composition containing hydrogen gas and a reactant that causes the liquid composition containing hydrogen gas to gel or thicken are mixed, and the first line mixer and the second line mixer are connected.

The production device according to the second embodiment of the present invention is preferably a production device for performing the production method according to the second embodiment of the present invention.

Figure 2:
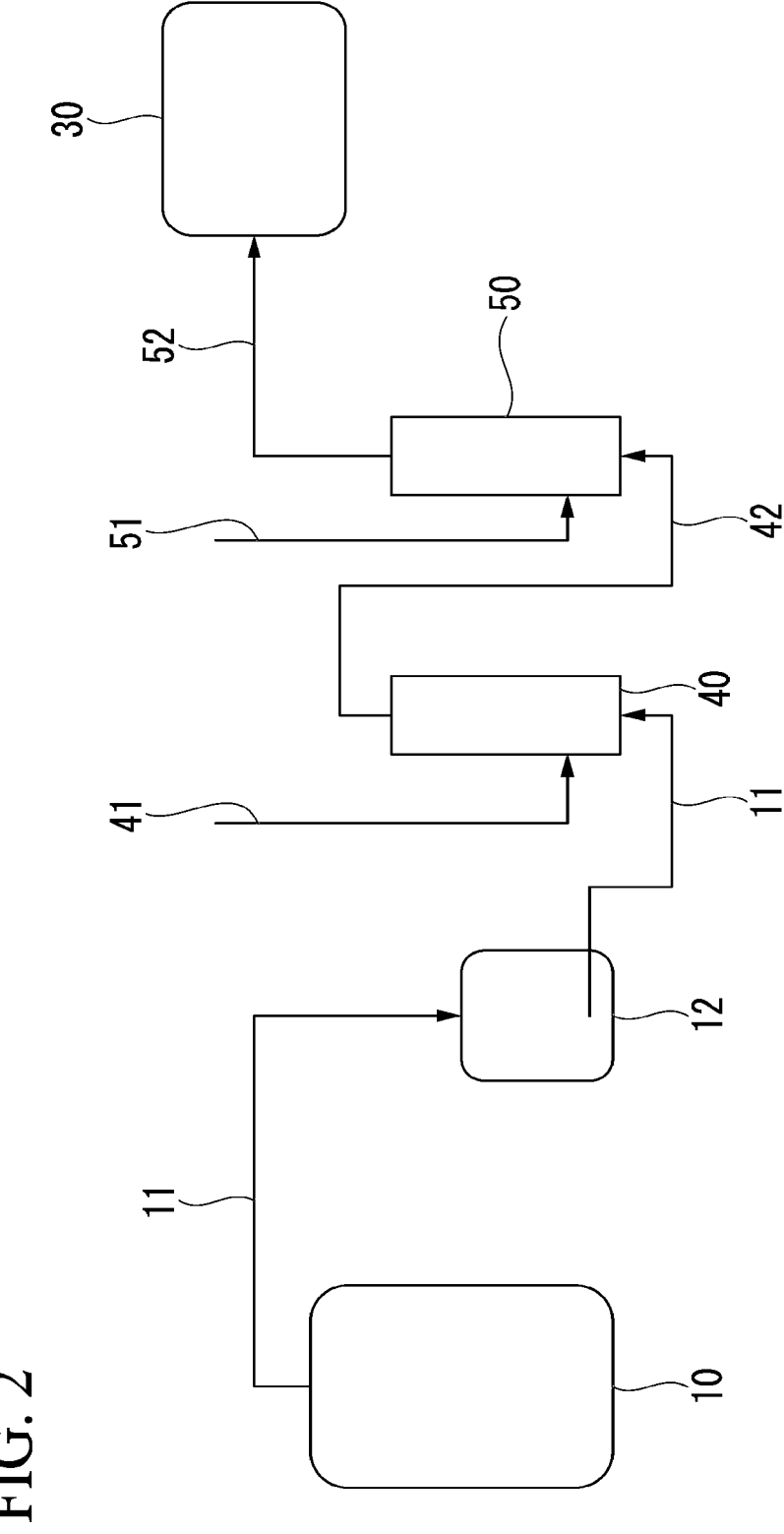
FIG. 2 is a schematic view illustrating a method for producing a hydrogen gas-containing material and a device for producing the same according to a second embodiment of the present invention.

FIG. 2 schematically shows a production device according to the second embodiment of the present invention as one aspect of the production device according to the second embodiment of the present invention. As shown in FIG. 2, the production device according to the second embodiment includes a preparation container 10 in which a liquid composition is prepared, a first line mixer 40 in which a liquid composition and hydrogen gas are mixed, a second line mixer 50 in which a liquid composition containing hydrogen gas and a reactant are mixed, and a filling device 30 in which a gel composition or a viscous composition as a hydrogen gas-containing material is filled into a filling container. A hydrogen supply pipe 41 through which hydrogen gas is supplied to the first line mixer 40 is connected to the first line mixer 40. A reactant supply pipe 51 through which a reactant is supplied to the second line mixer 50 is connected to the second line mixer 50.

A supply pipe 11 through which the liquid composition prepared in the preparation container 10 is supplied to the first line mixer 40 is provided between the preparation container 10 and the first line mixer 40. A liquid-transfer pipe 42 through which the liquid composition containing hydrogen gas mixed in in the first line mixer 40 is transferred as a liquid to the second line mixer 50 is provided between the first line mixer 40 and the second line mixer 50. A liquid-transfer pipe 52 through which the reactant and liquid composition containing hydrogen gas mixed in in the second line mixer 50, that is, the gel composition or the viscous composition, is transferred as a liquid to the filling device 30, is provided between the second line mixer 50 and the filling device 30, and the filling device 30 is connected to the end part of the liquid-transfer pipe 52. The pump 12 by which the liquid composition prepared in the preparation container 10 is transferred as a liquid to the first line mixer 40 is provided on the supply pipe 11.

First, in the second embodiment of the present invention, the liquid composition prepared in the preparation container 10 shown in FIG. 2 and hydrogen gas are mixed in in the first line mixer 40 (line mixing).

As the gelling agent or the thickener in the second embodiment of the present invention, those that cause a liquid composition to gel or thicken due to a reaction with a reactant are used. Specific examples of such a gelling agent or thickener include synthetic polymers such as a carboxyvinyl polymer, carboxyvinyl polymer derivatives, polyvinyl alcohol, polyvinyl alcohol derivatives, polyvinyl pyrrolidone, polyvinyl pyrrolidone derivatives, polyhydroxyethyl methacrylate, polyacrylic acid, polystyrene sulfonic acid, and silicones (dimethicone, cyclic dimethicone, methyl phenyl polysiloxane, crosslinked dimethylpolysiloxanc, methylsiloxane reticular polymers, polyether-modified silicones, acrylic-modified silicones, amethicone, etc.), alginates such as sodium alginate, potassium alginate, calcium alginate, and ammonium alginate, and alginic acid derivatives such as propylene glycol alginate ester, but not limited thereto.

Regarding such a gelling agent or thickener, one, two or more selected from among a carboxyvinyl polymer, carboxyvinyl polymer derivatives, polyvinyl alcohol, polyvinyl alcohol derivatives, polyvinyl pyrrolidone, polyvinyl pyrrolidone derivatives, polyhydroxyethyl methacrylate, polyacrylic acid, polystyrene sulfonic acid, silicones, alginate, and alginic acid derivatives are preferable, one, two or more selected from the group consisting of a carboxyvinyl polymer, carboxyvinyl polymer derivatives, polyvinyl alcohol, polyvinyl alcohol derivatives, polyvinyl pyrrolidone, polyvinyl pyrrolidone derivatives, polyacrylic acid, silicones, alginate, and alginic acid derivatives are more preferable, and a carboxyvinyl polymer is still more preferable.

In preparation of a liquid composition, a liquid medium such as water or an organic solvent is put into the preparation container 10, and raw materials containing a gelling agent or a thickener are then put thereinto while stirring, and heating can be performed to a temperature higher than a gelling temperature or a temperature at which thickening is prevented, but not limited thereto.

The preparation container 10 may be appropriately selected according to a gelling agent or thickener to be used. For example, it may be selected in consideration of the heat resistance of the container and the corrosion resistance with respect to the liquid composition. Examples of the member constituting the preparation container 10 include a device material such as an SUS material, a glass lining, a fluororesin lining, and a plastic, but not limited thereto.

When a liquid composition containing a gelling agent is used as the liquid composition in the second embodiment of the present invention, the temperature of the liquid composition is maintained at a temperature higher than a gelling temperature before mixing with hydrogen gas from preparation. On the other hand, when a liquid composition containing a thickener is used as the liquid composition, the temperature of the liquid composition is maintained at a temperature at which thickening is prevented before mixing with hydrogen gas from preparation.

The liquid composition prepared in the preparation container 10 is supplied to the first line mixer 40 via the supply pipe 11. In addition, hydrogen gas is supplied to the first line mixer 40 via the hydrogen supply pipe 41. Here, a method for supplying hydrogen gas to the first line mixer 40 is not particularly limited.

In the second embodiment of the present invention, as in the first embodiment, the pump 12 is used when the liquid composition is supplied from the preparation container 10 to the first line mixer 40. The pump 12 may be a known pump having a function of adjusting a pressure of a liquid composition that flows through the supply pipe 11 or may be a pressure pump or a decompression pump.

The liquid composition is supplied from the preparation container 10 to the first line mixer 40 via the supply pipe 11 using the pump 12, and thus an amount of hydrogen gas dispersed in the liquid composition containing hydrogen gas is easily controlled.

As in the first embodiment, the ratio between the volume of the liquid composition and the volume of hydrogen gas supplied to the first line mixer 40 is appropriately set according to a desired content of hydrogen gas of the hydrogen gas-containing material obtained in the method for producing a hydrogen gas-containing material of the present invention and a gelling agent or thickener to be used.

The ratio between the volume of the liquid composition and the volume of hydrogen gas supplied to the first line mixer 40 is preferably 0.01 to 2.0, more preferably 0.05 to 1.8, and still more preferably 0.1 to 1.5.

Here, "the ratio between the volume of the liquid composition and the volume of hydrogen gas supplied to the first line mixer 40" is a value obtained according to (flow rate of hydrogen gas)/(flow rate of the liquid composition supplied to the first line mixer 40).

Mixing of a liquid composition and hydrogen gas is preferably performed without exposing the liquid composition to outside air.

Regarding the first line mixer 40, a known line mixer having a function and form that can perform mixing without exposing the liquid composition and hydrogen gas to outside air can be used. As a specific example, a Homomic Line Flow 30 type which is a homo mixer (commercially available from PRIMIX Corporation) can he used, but not limited thereto.

Examples of such a line mixer include a static mixer that generates swirling and turbulence by providing an obstacle in the flow path, a homogenizer including a mechanism in which a movable part shears a fluid in the flow path, and a dynamic mixer such as a homo mixer, but not limited thereto. In addition, a pump having the same function may be used without limitation to those called a mixer. Such a mixer may be used alone or two or more thereof may be used in combination.

Regarding the line mixer, a static mixer or a dynamic mixer is preferable, and in consideration of support of a high-viscosity fluid, a dynamic mixer is more preferable and a homo mixer is still more preferable.

Next, in the second embodiment of the present invention, the liquid composition containing hydrogen gas and the reactant are mixed in in the second line mixer 50 and the liquid composition containing hydrogen gas gels or thickens. Preferably, the liquid composition containing hydrogen gas and the reactant are mixed without exposing the liquid composition containing hydrogen gas to outside air. In addition, preferably, liquid transfer of the liquid composition containing hydrogen gas from the first line mixer 40 to the second line mixer 50 is performed without exposing the liquid composition containing hydrogen gas to outside air.

More specifically, the liquid composition containing hydrogen gas supplied to the second line mixer 50 is mixed (line mixing) with the reactant supplied from the reactant supply pipe 51 to the second line mixer 50 in the second line mixer 50. The liquid composition containing hydrogen gas mixed in in the second line mixer 50 gels or thickens while hydrogen gas is contained due to the reactant. According to mixing with the reactant in the second line mixer 50, the liquid composition containing hydrogen gas becomes a gel composition containing hydrogen gas or a viscous composition containing hydrogen gas.

Regarding the second line mixer 50, a known line mixer having a function and form that can perform mixing without exposing the liquid composition containing hydrogen gas and the reactant to outside air can be used. As a specific example, a Homomic Line Flow 30 type which is a homo mixer (commercially available from PRIMIX Corporation) can be used, but not limited thereto.

Examples of such a line mixer include a static mixer that generates swirling and turbulence by providing an obstacle in the flow path, a homogenizer including a mechanism in which a movable part shears a fluid in the flow path, and a dynamic mixer such as a homo mixer, but not limited thereto. In addition, a pump having the same function may be used without limitation to those called a mixer.

Regarding the line mixer, a static mixer or a dynamic mixer is preferable, and in consideration of support of a high-viscosity fluid, a dynamic mixer is more preferable and a homo mixer is still more preferable.

Regarding the reactant that causes the liquid composition to gel or thicken, a known reactant having effects of promoting formation of a network structure due to a gelling agent or increase in the viscosity due to the thickener may be used. Specific examples thereof include a neutralizing agent and a crosslinking agent, but not limited thereto.

In particular, regarding the gelling agent or the thickener, when the aqueous solution containing a carboxyvinyl polymer gels or thickens, a neutralizing agent is preferably used as the reactant.

As the neutralizing agent, a known neutralizing agent can be used. Specific examples thereof include hydroxides such as sodium hydroxide and potassium hydroxide, fatty acid amines such as triethanolamine, an ammonia compound, and a carbonate compound, but not limited thereto.

On the other hand, a known crosslinking agent can be used as the crosslinking agent. Specific examples thereof include carbodiimide, N-hydroxy ester, imide ester, maleimide, haloacetyl, pyridyl disulfide, hydrazide, and alkoxyamine, but not limited thereto.

In addition, the concentration and type of the reactant are appropriately selected according to a gelling agent or thickener to be used.

The gel composition containing hydrogen gas or viscous composition containing hydrogen gas obtained by gelling or thickening is supplied to the filling device 30 connected to the end part of the liquid-transfer pipe 52 and filled in the filling container by the filling device 30. When the filling device 30 is connected to the end part of the liquid-transfer pipe 52, it is easy to prevent a gas other than hydrogen gas from being mixed into the gel composition containing hydrogen gas or the viscous composition containing hydrogen gas.

Liquid transfer of the gel composition containing hydrogen gas or the viscous composition containing hydrogen gas from the second line mixer 50 to the filling device 30 is preferably performed without exposing the gel composition containing hydrogen gas or the viscous composition containing hydrogen gas to outside air.

Details of a material of a filling container to be used, a filling method, and a method for sealing a filling container, and preferable modes are the same as those in the above first embodiment.

(Actions and Effects of the Second Embodiment)

As described above, in the method according to the second embodiment of the present invention, a liquid composition and hydrogen gas are mixed in in a first line mixer, a liquid composition containing hydrogen gas and a reactant are mixed in in a second line mixer, and gelling or thickening is caused. Therefore, since hydrogen gas does not leak to the outside air, a ratio between hydrogen gas and oxygen gas in the gas phase around the device is not within an explosive range, and a risk of fire is significantly reduced. In addition, since hydrogen gas is mixed in in the line mixer, an amount of an unnecessary gas containing nitrogen gas mixed into the hydrogen gas-containing material is reduced and the quality of the hydrogen gas-containing material is improved. In addition, since there is no need to provide a gas sensor, mixing is performed in a line mixer for a short time, and a hydrogen gas-containing material can be continuously produced, it is possible to produce a hydrogen gas-containing material simply and efficiently according to a production method in the related art and it is easy to control an amount of hydrogen contained in the hydrogen gas-containing material.

[Method for Producing a Hydrogen Gas-Containing Material and Device for Producing the Same According to Other Embodiment]

A method for producing a hydrogen gas-containing material of the present invention is not limited to those described in the above first embodiment and second embodiment. For example, in the first embodiment, the liquid composition in the liquid-transfer pipe 22 may be cooled and gelled or thickened by naturally releasing heat at room temperature without providing the cooler 23 in the liquid-transfer pipe 22. In addition, hydrogen gas mixed in the first embodiment and the second embodiment may contain other gases as long as the effects of the present invention are not impaired.

In addition, regarding mixing of a liquid composition and hydrogen gas, a liquid composition obtained by mixing a gelling agent or a thickener and a liquid medium in in a line mixer (the line mixer 20 in the first embodiment or the first line mixer 40 in the second embodiment) may be mixed with hydrogen gas in the line mixer (the line mixer 20 in the first embodiment or the first line mixer 40 in the second embodiment). In addition, when the gelling agent or the thickener and the liquid medium are mixed to prepare a liquid composition, it may be circulated through a circulation path including the line mixer (the line mixer 20 in the first embodiment or the first line mixer 40 in the second embodiment) for mixing and thereby a liquid composition may he obtained.

Figure 3:
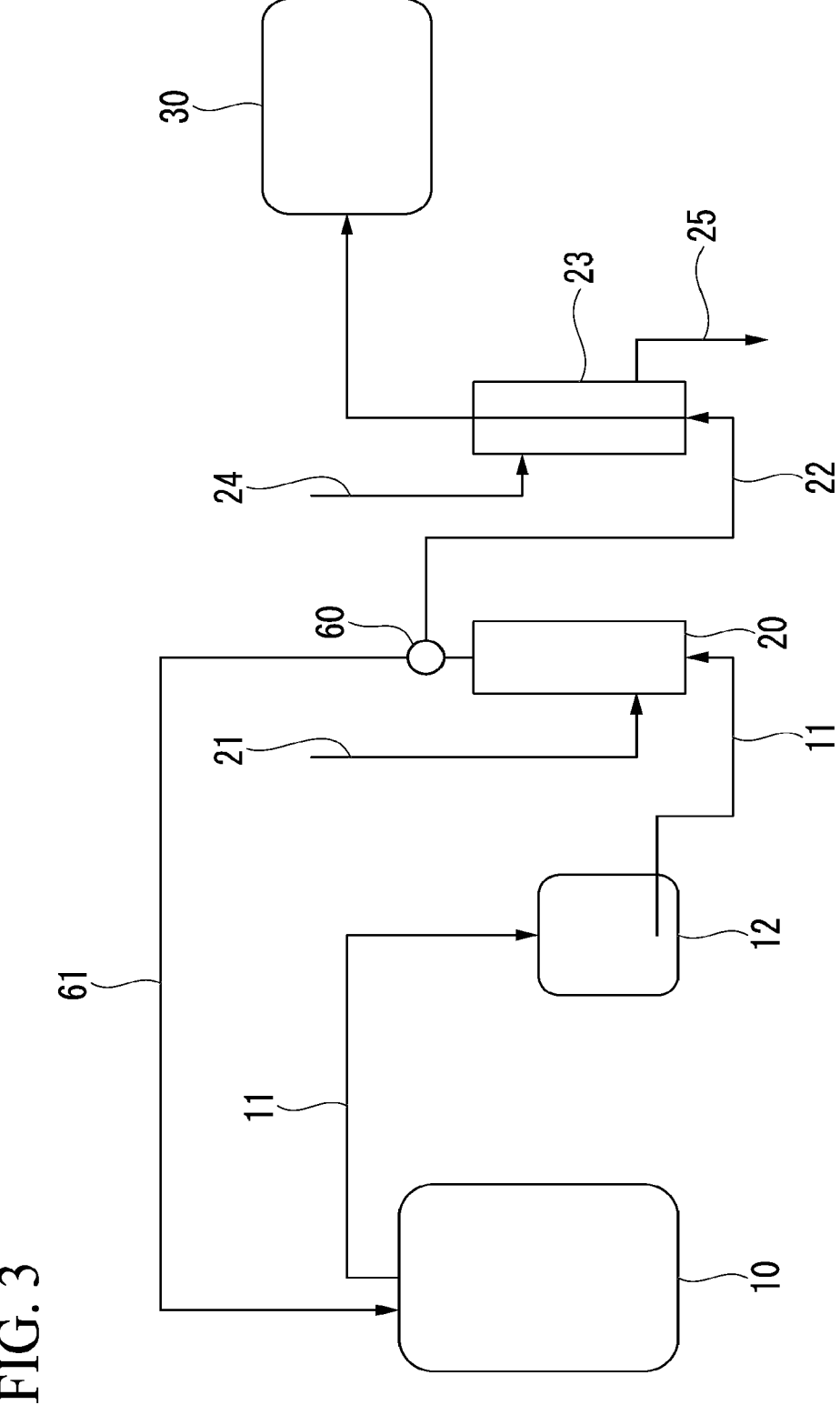
FIG. 3 is a schematic view illustrating a modified example of the method for producing a hydrogen gas-containing material and the device for producing the same according to the first embodiment of the present invention.

A specific mode will be described with reference to FIG. 3 showing a modified example of the first embodiment.

Here, the same modified example can also be applied to the second embodiment of the present invention. In this case, in the following description, "the line mixer 20" can be replaced with "the first line mixer 40", and "the liquid-transfer pipe 22" can be replaced with "the liquid-transfer pipe 42" for application.

The production device in FIG. 3 includes a return line 61 that causes a liquid composition composed of the gelling agent or thickener and the liquid medium mixed in in the line mixer 20 to be circulated in the preparation container 10. In addition, the production device in FIG. 3 includes a line switching unit 60 configured to switch between liquid transfer of the liquid composition composed of the gelling agent or thickener and the liquid medium mixed in in the line mixer 20 to the return line 61 and liquid transfer of the liquid composition containing hydrogen gas mixed in in the line mixer 20 to the liquid-transfer pipe 22.

The line switching unit 60 may be installed near the exit on the side of the liquid-transfer pipe 22 of the line mixer 20, and may be installed on a part of the liquid-transfer pipe 22 which is positioned on the side of the line mixer 20 with respect to the cooler 23. The return line 61 connects the line switching unit 60 and the preparation container 10. In addition, the return line 61 forms a circulation path together with the preparation container 10, the supply pipe 11 including the pump 12, the line mixer 20, and in some cases, a part of the liquid-transfer pipe 22, and the line switching unit 60. In the present invention, the cooler 23 (the second line mixer 50 in the application to the second embodiment) is not included in the circulation path.

In this modified example, for example, a mixture in which a gelling agent or a thickener and a liquid medium are mixed in in the preparation container 10 is supplied to the line mixer 20 via the supply pipe 11, and mixing is performed in the line mixer 20 when hydrogen gas is not supplied, liquid transfer is performed to the return line 61 via the line switching unit 60, the liquid composition is caused to circulate in the preparation container 10, and thus the mixture of the gelling agent or the thickener and the liquid medium is caused to circulate through the circulation path and mixing is performed and thereby a liquid composition can be prepared. When the liquid composition is sufficiently mixed, hydrogen gas is supplied to the line mixer 20, the liquid composition and hydrogen gas are mixed in in the line mixer 20, the line switching unit 60 is switched from the side of the circulation path to the side of the liquid-transfer pipe 22, and thus the liquid composition containing hydrogen gas can he transferred as a liquid to the liquid-transfer pipe 22.

The line mixer in which a liquid composition is mixed may be used together with a line mixer for dispersing hydrogen gas or may be separately provided in the front or rear stage of a line mixer for dispersing hydrogen gas.

[Application of Hydrogen Gas-Containing Material]

The hydrogen gas-containing material obtained by the method for producing a hydrogen gas-containing material of the present invention and the hydrogen gas-containing material obtained by the device for producing a hydrogen gas-containing material of the present invention are particularly suitably used in the industrial fields of foods, cosmetics, medicines, livestock, aquaculture, and cell cultures.

EXAMPLES

The present invention will be described below in detail with reference to examples, but not limited thereto.

Example 1

7 kg of gelatin and 13 kg of water were put into the preparation container 10 shown in FIG. 1 and heated at 40° C. to obtain a liquid composition containing gelatin. The obtained liquid composition was transferred as a liquid by pressurizing with the pump 12 (sine pump MR-115 type commercially available from WATSON MARLOW Co., Ltd), and supplied to the line mixer 20 (Homomic Line Flow 30 type commercially available from PRIMIX Corporation), and mixed with hydrogen gas supplied from the hydrogen supply pipe 21 in the line mixer 20. In the liquid-transfer pipe connected to the line mixer 20, the liquid composition mixed with hydrogen gas was cooled to obtain a gel composition (viscous composition) containing hydrogen gas in a bubble state. A content of hydrogen gas in a bubble state in the obtained gel composition (viscous composition) was measured by gas chromatography and the result was 30 volume % (v/w).

A concentration of hydrogen gas around the production device was measured using a gas detection tube (hydrogen gas detection tube commercially available from Gastec Corporation) and the concentration of hydrogen gas was equal to or less than 0.5% (detection limit).

Example 2

0.1 kg of a carboxyvinyl polymer (Carbopol (registered trademark) 980 commercially available from CBC Co., Ltd), 0.1 kg of a high-molecular-weight emulsifier (PEMULEN (registered trademark) commercially available from Nikko Chemicals Co., Ltd.) and 19.8 kg of water were put into the preparation container 10 shown in FIG. 2 to obtain a liquid composition containing a carboxyvinyl polymer. The obtained liquid composition was transferred as a liquid by pressurizing with the pump 12 (sine pump MR-115 type commercially available from WATSON MARLOW Co., Ltd), and supplied to the first line mixer 40 (Homomic Line Flow 30 type commercially available from PRIMIX Corporation), and mixed with hydrogen gas supplied from the hydrogen supply pipe 41 in the first line mixer 40. The liquid composition mixed with hydrogen gas was supplied to the second line mixer 50 and mixed with the reactant (10% sodium hydroxide aqueous solution) supplied from the reactant supply pipe 51 in the second line mixer 50 to obtain a gel composition (viscous composition) containing hydrogen gas in a bubble state. A content of hydrogen gas in a bubble state in the obtained gel composition (viscous composition) was measured by gas chromatography and the result was 40 volume % (v/w).

A concentration of hydrogen gas around the production device was measured using a gas detection tube (hydrogen gas detection tube commercially available from Gastec Corporation) and the concentration of hydrogen gas was equal to or less than 0.5% (detection limit).

Example 3

<Raw Materials>
(Liquid A)

Preservative 1: ethylhexyl glycerin (commercially available from Schulke & Mayr GmbH (obtained from Seiwa Kasei Co., Ltd.), SENSIVA (registered trademark) SC50JP).

Preservative 2: phenoxyethanol (phenoxyethanol-S commercially available from Yokkaichi Chemical Co., Ltd.).

Moisturizing component 1: concentrated glycerin (concentrated glycerin for cosmetics commercially available from Sakamoto Yakuhin Kogyo Co., Ltd.).

Surfactant 1: sucrose stearate (Surfhope (registered trademark) SE COSME C-1811 commercially available from Mitsubishi-Chemical Foods Corporation).

Alkaline agent 1: 10 mass % potassium hydroxide aqueous solution (potassium hydroxide commercially available from Wako Pure Chemical Corporation).
(Liquid B)

Wax 1: jojoba oil (NIKKOL (registered trademark) jojoba oil S commercially available from Nikko Chemicals Co., Ltd.).

Fats and oils 1: meadowfoam oil (containing a small amount of antioxidant tocopherol) (CROPURE (registered trademark) MEADOWFOAM-LQ-(JP) commercially available from CRODA JAPAN KK).

Fats and oils 2: shea oil (including a small amount of antioxidant tocopherol) (CROPURE (registered trademark) SHEA BUTTER-SO-(JP) commercially available from CRODA JAPAN KK).

Higher alcohol 1: behenyl alcohol (Kalcol (registered trademark) 220-80 commercially available from Kao Corporation).

Higher alcohol 2: stearyl alcohol (Kalcol (registered trademark) 8688 commercially available from Kao Corporation).

Higher alcohol 3: cetyl alcohol (Kalcol (registered trademark) 6098 commercially available from Kao Corporation).

Fatty acid 1: stearic acid (Lunac (registered trademark) S-70V commercially available from Kao Corporation).

5 g of the preservative 1, 20 g of the preservative 2, 400 g of the moisturizing component 1, 100 g of the surfactant 1, 15 g of the alkaline agent 1 and 3932.5 g of water were put into the preparation container 10 shown in FIG. 3 to obtain Liquid A composed of aqueous components. 175 g of the wax 1, 100 g of the fats and oils 1, 2.5 g of the fats and oils 2, 50 g of the higher alcohol 1, 50 g of the higher alcohol 2, 50 g of the higher alcohol 3, and 100 g of the fatty acid 1 were put into another container to obtain Liquid B composed of oily components. Each of the Liquid A and the Liquid B was heated to 70° C., and liquid transfer was then performed by pressurizing with the pump 12 (sine pump MR-115 type commercially available from WATSON MARLOW Co., Ltd) while the Liquid B was gradually added to the Liquid A of the preparation container 10, and supply was performed to the line mixer 20 (Homomic Line Flow 30 type commercially available from PRIMIX Corporation) while hydrogen gas was not supplied, the line switching unit 60 installed on the exit side of the line mixer was switched so that liquid transfer was performed to the side of the return line 61, and the mixture containing the Liquid A and the Liquid B was caused to circulate through a circulation path including the return line 61, the preparation container 10, the supply pipe 11, and the line mixer 20. In order to emulsify the mixture containing the Liquid A and the Liquid B, it was caused to circulate through the circulation path for 30 minutes and then cooled to 55° C. Hydrogen gas was supplied to the line mixer 20 and mixed with hydrogen gas supplied from the hydrogen supply pipe 21 in the line mixer 20, the line switching unit 60 installed on the exit side of the line mixer was switched so that liquid transfer was performed to the side of the liquid-transfer pipe 22, and the liquid composition mixed with hydrogen gas was cooled in the liquid-transfer pipe 22 connected to the line mixer 20 to obtain a gel composition (viscous composition) containing hydrogen gas in a bubble state. A content of hydrogen gas in a bubble state in the obtained gel composition (viscous composition) was measured by gas chromatography and the result was 57 volume % (v/w).

A concentration of hydrogen gas around the production device was measured using a gas detection tube (hydrogen gas detection tube commercially available from Gastec Corporation) and the concentration of hydrogen gas was equal to or less than 0.5% (detection limit).

Comparative Example 1

A liquid composition containing gelatin was prepared as in Example 1. In the container for preparation, the obtained liquid composition and hydrogen gas were mixed. Then, the liquid composition mixed with hydrogen gas was cooled to obtain a gel composition (viscous composition) containing hydrogen gas in a bubble state.

A concentration of hydrogen gas around the container for preparation was measured in a gas detection tube (hydrogen gas detection tube commercially available from Gastec Corporation) and 0.5% (detection limit) or more of hydrogen gas was detected.

Comparative Example 2

A liquid composition containing a carboxyvinyl polymer was prepared as in Example 2. The obtained liquid composition and hydrogen gas were mixed in in the container for preparation. Then, the liquid composition mixed with hydrogen gas and the reactant (10% sodium hydroxide aqueous solution) were mixed in in the container for preparation to obtain a gel composition (viscous composition).

A concentration of hydrogen gas around the container for preparation was measured in a gas detection tube (hydrogen gas detection tube commercially available from Gastec Corporation) and 0.5% (detection limit) or more of hydrogen gas was detected.

REFERENCE SIGNS LIST

10 Preparation container
11 Supply pipe

12 Pump
20 Line mixer
21 Hydrogen supply pipe
22 Liquid-transfer pipe
23 Cooler
24 Cooling liquid supply pipe
25 Cooling liquid discharge pipe
30 Filling device
40 First line mixer
41 Hydrogen supply pipe
42 Liquid-transfer pipe
50 Second line mixer
51 Reactant supply pipe
52 Liquid-transfer pipe
60 Line switching unit
61 Return line

The invention claimed is:

1. A method for producing a hydrogen gas-containing material, the method comprising:
   mixing a first liquid composition with a hydrogen gas in a line mixer, thereby producing a second liquid composition comprising the hydrogen gas, wherein the first liquid composition and the second liquid composition are both in liquid state;
   cooling the second liquid composition in a liquid-transfer pipe connected to the line mixer and causing the second liquid composition to gel or thicken, thereby forming the hydrogen gas-containing material; and
   filling the hydrogen gas-containing material into a filling container at an end part of the liquid-transfer pipe;
   wherein the mixing, the cooling, and the filling are performed without exposing to outside air,
   wherein the first liquid composition comprises:
   a liquid medium; and
   a gelling agent or thickener,
   wherein the mixing is at a first temperature that is higher than a gelling temperature of the gelling agent when the first liquid composition comprises the gelling agent, and higher than a temperature at which thickening is prevented in the thickener when the first liquid composition comprises the thickener, and
   wherein the cooling is to a second temperature that is lower than the gelling temperature of the gelling agent when the first liquid composition comprises the gelling agent, and lower than the temperature at which thickening is prevented in the thickener when the first liquid composition comprises the thickener.

2. The method according to claim 1,
   wherein the second liquid composition in the liquid-transfer pipe is further cooled using an additional cooler.

3. The method according to claim 1,
   wherein the first liquid composition is transferred as a liquid to the line mixer using a pump.

4. The method according to claim 1, further comprising:
   preparing the first liquid composition by mixing the gelling agent or the thickener, and the liquid medium in the line mixer prior to the mixing with the hydrogen gas.

5. The method according to claim 4, further comprising:
   circulating the first liquid composition through a circulation path including the line mixer prior to the mixing with the hydrogen gas.

6. The method according to claim 1, wherein:
   the liquid-transfer pipe has a first end directly connected to the line mixer and a second end directly connected to the filling container.

7. The method according to claim 1, wherein:

the first liquid composition comprises the gelling agent, the mixing is at the first temperature that is higher than the gelling temperature of the gelling agent, and the cooling is to the second temperature that is lower than the gelling temperature of the gelling agent.

8. A device for producing a hydrogen gas-containing material, the device comprising:

a line mixer for mixing a first liquid composition with a hydrogen gas, thereby producing a second liquid composition comprising the hydrogen gas, wherein the first liquid composition and the second liquid composition are both in liquid state;

a liquid-transfer pipe connected to the line mixer;

a cooler for cooling the second liquid composition in the liquid-transfer pipe connected to the line mixer and causing the second liquid composition to gel or thicken, thereby forming the hydrogen gas-containing material;

a filling container at an end part of the liquid-transfer pipe; and a filling device for filling the hydrogen gas-containing material into the filling container at the end part of the liquid-transfer pipe, wherein the mixing, the cooling, and the filling are performed without exposing to outside air, wherein the first liquid composition comprises:

a liquid medium; and a gelling agent or thickener, wherein the mixing is at a first temperature that is higher than a gelling temperature of the gelling agent when the first liquid composition comprises the gelling agent, and higher than a temperature at which thickening is prevented in the thickener when the first liquid composition comprises the thickener, and wherein the cooling is to a second temperature that is lower than the gelling temperature of the gelling agent when the first liquid composition comprises the gelling agent, and lower than the temperature at which thickening is prevented in the thickener when the first liquid composition comprises the thickener.

9. The device according to claim 8, further comprising:

a pump that transfers the first liquid composition as a liquid to the line mixer.

10. The device according to claim 8, wherein:

the filling device is connected to the end part of the liquid-transfer pipe.

11. The device according to claim 8, wherein:

the line mixer is in a circulation path.

12. The device according to claim 11, further comprising:

a line switching unit for switching liquid transfer to the circulation path to liquid transfer to the liquid-transfer pipe.

* * * * *